US008623034B2

(12) United States Patent
Priewe

(10) Patent No.: US 8,623,034 B2
(45) Date of Patent: Jan. 7, 2014

(54) SOFT TISSUE REPAIR IMPLANT

(75) Inventor: Joerg Priewe, Kiel (DE)

(73) Assignee: Ethicon, GmbH, Norderstedt (DE)

( * ) Notice: Subject to any disclaimer, the term of this patent is extended or adjusted under 35 U.S.C. 154(b) by 1039 days.

(21) Appl. No.: 11/875,079

(22) Filed: Oct. 19, 2007

(65) Prior Publication Data
US 2009/0105731 A1 Apr. 23, 2009

(51) Int. Cl.
A61B 17/08 (2006.01)
(52) U.S. Cl.
USPC ........... 606/151; 606/213; 623/23.72; 600/37
(58) Field of Classification Search
USPC ................ 606/151; 623/23.72, 23.7, 23.764, 623/23.74, 23.76; 600/29, 30, 37
See application file for complete search history.

(56) References Cited

U.S. PATENT DOCUMENTS

| 3,182,662 | A | 5/1965 | Shirodkar |
| 3,212,502 | A | 10/1965 | Myers |
| 3,311,110 | A | 3/1967 | Singerman et al. |
| 3,372,696 | A | 3/1968 | Beliveau et al. |
| 3,472,232 | A | 10/1969 | Earl |
| 3,608,095 | A | 9/1971 | Barry |
| 3,763,860 | A | 10/1973 | Clarke |
| 3,858,783 | A | 1/1975 | Kapitanov et al. |
| 3,924,633 | A | 12/1975 | Cook et al. |
| 4,037,603 | A | 7/1977 | Wendorff |
| 4,128,100 | A | 12/1978 | Wendorff |
| 4,235,238 | A | 11/1980 | Ogiu et al. |
| 4,392,495 | A | 7/1983 | Bayers |
| 4,441,497 | A | 4/1984 | Paudler |
| 4,509,516 | A | 4/1985 | Richmond |
| 4,549,545 | A | 10/1985 | Levy |
| 4,655,221 | A | 4/1987 | Devereux |

(Continued)

FOREIGN PATENT DOCUMENTS

| AU | 278089 | 9/1967 |
| AU | 441561 | 10/1973 |

(Continued)

OTHER PUBLICATIONS

Petros. "Vault Prolapse I: Dynamic Supports of the Vagina", International Urogynecol Journal. vol. 12, (2001), pp. 292-295.

(Continued)

Primary Examiner — Corrine M McDermott
Assistant Examiner — Jing Ou
(74) Attorney, Agent, or Firm — Greenberg Traurig

(57) ABSTRACT

A soft tissue repair implant includes a body having a base section and at least one appendage extending outwardly from the base section. The body is flexible such that the at least one appendage is movable relative to the base section. More particularly, the body is collapsible to a substantially planar configuration, in which the at least one appendage is positioned substantially co-planar relative to the base section. The body is also expandable to a substantially three-dimensional configuration, in which the at least one appendage extends at an angle from the base section. The body is constructed from a single, one-piece sheet such that the at least one appendage is connected to the base section seamlessly without any joint therebetween. A method for making the implant includes the steps of providing a flexible one-piece sheet, making a plurality of cuts in the sheet so as to form the body, and removing portions of the sheet beyond an outer periphery of the body.

11 Claims, 4 Drawing Sheets

(56) References Cited

U.S. PATENT DOCUMENTS

| | | | |
|---|---|---|---|
| 4,946,467 A | 8/1990 | Ohi et al. | |
| 5,013,292 A | 5/1991 | Lemay | |
| 5,032,508 A | 7/1991 | Naughton et al. | |
| 5,080,667 A | 1/1992 | Chen et al. | |
| 5,112,344 A | 5/1992 | Petros | |
| 5,180,385 A | 1/1993 | Sontag | |
| 5,250,033 A | 10/1993 | Evans et al. | |
| 5,281,237 A | 1/1994 | Gimpelson | |
| 5,337,736 A | 8/1994 | Reddy | |
| 5,362,294 A | 11/1994 | Seitzinger | |
| 5,368,595 A | 11/1994 | Lewis | |
| 5,368,756 A | 11/1994 | Vogel et al. | |
| 5,382,257 A | 1/1995 | Lewis et al. | |
| 5,383,904 A | 1/1995 | Totakura et al. | |
| 5,403,328 A | 4/1995 | Shallman | |
| 5,441,508 A | 8/1995 | Gazielly et al. | |
| 5,450,860 A | 9/1995 | O'Connor | |
| 5,480,436 A | 1/1996 | Bakker et al. | |
| 5,507,796 A | 4/1996 | Hasson | |
| 5,582,188 A | 12/1996 | Benderev et al. | |
| 5,611,515 A | 3/1997 | Benderev et al. | |
| 5,628,756 A | 5/1997 | Barker, Jr. et al. | |
| 5,645,568 A | 7/1997 | Chervitz et al. | |
| 5,741,299 A | 4/1998 | Rudt | |
| 5,816,258 A | 10/1998 | Jervis | |
| 5,836,315 A | 11/1998 | Benderev et al. | |
| 5,840,011 A | 11/1998 | Landgrebe et al. | |
| 5,855,549 A | 1/1999 | Newman | |
| 5,860,425 A | 1/1999 | Benderev et al. | |
| 5,899,909 A | 5/1999 | Claren et al. | |
| 5,922,026 A | 7/1999 | Chin | |
| 5,934,283 A | 8/1999 | Willem et al. | |
| 5,935,122 A | 8/1999 | Fourkas et al. | |
| 5,997,554 A | 12/1999 | Thompson | |
| 6,010,447 A | 1/2000 | Kardjian | |
| 6,030,393 A | 2/2000 | Corlew | |
| 6,042,534 A | 3/2000 | Gellman et al. | |
| 6,110,101 A | 8/2000 | Tihon et al. | |
| 6,117,067 A | 9/2000 | Gil-Vernet | |
| 6,197,036 B1 | 3/2001 | Tripp et al. | |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,334,446 B1 | 1/2002 | Beyar | |
| 6,382,214 B1 | 5/2002 | Raz et al. | |
| 6,406,423 B1 | 6/2002 | Scetbon | |
| 6,475,139 B1 | 11/2002 | Miller | |
| 6,491,703 B1 | 12/2002 | Ulmsten | |
| 6,575,897 B1 | 6/2003 | Ory et al. | |
| 6,605,097 B1 | 8/2003 | Lehe et al. | |
| 6,612,977 B2 | 9/2003 | Staskin et al. | |
| 6,669,735 B1 | 12/2003 | Pelissier | |
| 6,691,711 B2 | 2/2004 | Raz et al. | |
| 6,712,859 B2 * | 3/2004 | Rousseau et al. | 623/23.64 |
| 6,808,486 B1 | 10/2004 | O'Donnell | |
| 6,932,759 B2 | 8/2005 | Kammerer et al. | |
| 7,070,558 B2 | 7/2006 | Gellman et al. | |
| 7,083,637 B1 | 8/2006 | Tannhauser | |
| 7,087,065 B2 | 8/2006 | Ulmsten et al. | |
| 7,131,943 B2 | 11/2006 | Kammerer | |
| 7,179,224 B2 | 2/2007 | Willis | |
| 2001/0018549 A1 | 8/2001 | Scetbon | |
| 2001/0049467 A1 | 12/2001 | Lehe et al. | |
| 2002/0028980 A1 | 3/2002 | Thierfelder et al. | |
| 2002/0058959 A1 | 5/2002 | Gellman | |
| 2002/0077526 A1 | 6/2002 | Kammerer et al. | |
| 2002/0091373 A1 | 7/2002 | Berger | |
| 2002/0116070 A1 | 8/2002 | Amara et al. | |
| 2002/0183588 A1 | 12/2002 | Fierro | |
| 2002/0188169 A1 | 12/2002 | Kammerer et al. | |
| 2003/0004395 A1 | 1/2003 | Therin | |
| 2003/0023138 A1 | 1/2003 | Luscombe | |
| 2003/0069469 A1 | 4/2003 | Li | |
| 2003/0100954 A1 | 5/2003 | Schuldt-Hempe et al. | |
| 2003/0149440 A1 | 8/2003 | Kammerer et al. | |
| 2003/0195386 A1 | 10/2003 | Thierfelder et al. | |
| 2003/0212460 A1 * | 11/2003 | Darois et al. | 623/23.64 |
| 2003/0220538 A1 * | 11/2003 | Jacquetin | 600/37 |
| 2004/0039246 A1 * | 2/2004 | Gellman et al. | 600/30 |
| 2004/0039453 A1 | 2/2004 | Anderson et al. | |
| 2005/0070829 A1 * | 3/2005 | Therin et al. | 602/1 |
| 2005/0192600 A1 | 9/2005 | Nicolo et al. | |
| 2005/0240075 A1 | 10/2005 | Li | |
| 2005/0245787 A1 | 11/2005 | Cox et al. | |
| 2005/0250978 A1 * | 11/2005 | Kammerer | 600/29 |
| 2005/0278037 A1 * | 12/2005 | Delorme et al. | 623/23.72 |
| 2006/0195010 A1 * | 8/2006 | Arnal et al. | 600/30 |
| 2007/0225804 A1 | 9/2007 | Checa Ayet | |
| 2008/0147200 A1 * | 6/2008 | Rousseau et al. | 623/23.75 |

FOREIGN PATENT DOCUMENTS

| | | |
|---|---|---|
| DE | 3223153 | 8/1983 |
| DE | 4220283 | 12/1993 |
| DE | 4334419 A1 | 4/1995 |
| EP | 0668056 A1 | 8/1995 |
| EP | 0774240 A1 | 5/1997 |
| EP | 0 898 944 A2 | 3/1999 |
| EP | 0941712 A1 | 9/1999 |
| EP | 0598976 B1 | 7/2000 |
| EP | 1025811 A2 | 8/2000 |
| EP | 1238638 A1 | 9/2002 |
| EP | 0 898 944 B1 | 5/2004 |
| EP | 2209438 A1 | 7/2010 |
| GB | 2430372 A | 3/2007 |
| SE | 503271 C2 | 4/1996 |
| WO | 90/03766 | 4/1990 |
| WO | 96/06567 | 3/1996 |
| WO | 97/13465 | 4/1997 |
| WO | 98/31301 | 7/1998 |
| WO | 98/35632 | 8/1998 |
| WO | 01/06951 A1 | 2/2001 |
| WO | 02/19944 A2 | 3/2002 |
| WO | 02/28312 A1 | 4/2002 |
| WO | 02/38079 A2 | 5/2002 |
| WO | 01/39670 A1 | 6/2002 |
| WO | 03/092546 A2 | 11/2003 |
| WO | 2004/012626 A1 | 2/2004 |
| WO | WO 2004/012627 A1 | 2/2004 |
| WO | 2004/067056 A2 | 8/2004 |
| WO | WO 2004/071349 A2 | 8/2004 |
| WO | WO 2007104863 A2 | 9/2007 |
| WO | 2009/049910 A1 | 4/2009 |

OTHER PUBLICATIONS

Petros, "Vault Prolapse II: Restoration of Dynamic Vaginal Supports by Infracoccygeal Sacropexy, an Axial Day-Case Vaginal Procedure", International Urogynecol Journal, vol. 12, (2001), pp. 263-303.

Petros et al., "An Integral Theory for the Diagnosis and Management of Female Urinary Incontinence", Scandinavian Journal of Urology and Nephrology, Supplement 153, (1993), pp. 1-93.

"TVT Tension-free Vaginal Tape, Minimally Invasive Highly Effective Treatment for Female Stress Urinary Incontinence", Gynecare, Ethicon, Inc., 1999, pp. 1-6.

"AMS SPARC Sling System", American Medical Systems, Inc., Minnetonka, MN, (2001), pp. 1-6.

Gilberti, "Transvaginal Sacrospinous Colpopexy by Palpation—A New Minimally Invasive Procedure Using an Anchoring System", Adult Urology, vol. 57. (2001), pp. 666-668.

Cosson et al., "Cystocele Repair by Vaginal Patch, Short-term Results in 47 patients", Progres en Urologie, vol. II, (2001), pp. 340-346.

Collinet et al., "The Vaginal Patch for Vaginal Cure of Cystocele", J. Gynecol. Obstet. Biol. Reprod., vol. 29, No. 2, (2000), pp. 197-201.

Leanza et al., "New Technique for Correcting Both Incontinence and Cystocele: T.I.C.T.", Urogynaecologia International Journal, vol. 15, No. 3, (2001), pp. 133-140.

International Search Report and Written Opinion for corresponding International Patent Application No. PCT/EP2008/008865, mailed Feb. 2, 2009.

* cited by examiner

SOFT TISSUE REPAIR IMPLANT

FIELD OF THE INVENTION

The present invention relates to implants, and, more particularly, to soft tissue repair implants.

BACKGROUND OF THE INVENTION

In the past, various hernia implants have been developed (see, for instance, U.S. Pat. No. 6,669,735, U.S. Patent Publication No. 20050192600, European Patent Publication No. 0898944 B1 and International Patent Publication Nos. WO 2004071349 and WO 2004012627). Such implants are adapted to be implanted in patients through surgical procedures for repairing hernia defects.

SUMMARY OF THE INVENTION

The present invention relates to a soft tissue repair implant which includes a body having a base section and at least one appendage extending outwardly from the base section. The body is flexible such that the appendage is movable relative to the base section. More particularly, the body is collapsible to a substantially planar configuration, in which the appendage is positioned substantially co-planar relative to the base section. The body is also expandable to a substantially three-dimensional configuration, in which the appendage extends at an angle from the base section. The appendage is sized and shaped so as to be affixed to a tissue to secure the body to a repair site. The body is constructed from a single, one-piece sheet such that the appendage is connected to the base section seamlessly without any joint therebetween. In one embodiment of the present invention, the body includes at least two appendages.

In accordance with the present invention, a method for making the implant described above includes the steps of providing a flexible one-piece sheet, making a plurality of cuts in the sheet so as to form the body, and removing portions of the sheet beyond an outer periphery of the body.

BRIEF DESCRIPTION OF THE DRAWINGS

For a more complete understanding of the present invention, reference is made to the following detailed description of exemplary embodiments considered in conjunction with the accompanying drawings, in which.

DETAILED DESCRIPTION OF THE INVENTION

Figure 1:
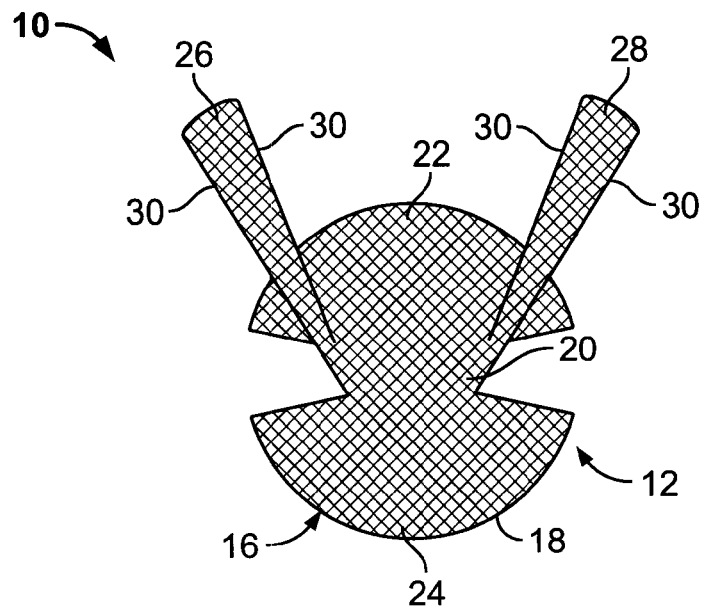
FIG. 1 is a perspective view of a hernia repair implant constructed in accordance with a first embodiment of the present invention, the implant being shown in its three-dimensional configuration.

FIG. 1 illustrates a hernia repair implant 10 constructed in accordance with a first embodiment of the present invention. The implant 10 has a body 12 constructed in its entirety from a single one-piece, two-dimensional (i.e., substantially flat or planar) sheet 14 (see FIG. 4) which is cut into a predetermined shape to form the body 12. As will be discussed in greater detail below, the body 12 is constructed such that it is collapsible into a two-dimensional configuration and is expandable into a three-dimensional configuration for implantation in a patient. Although the implant 10 of the present invention is adapted for use in repairing any type of hernia defect, as well as other types of soft tissue defect, it is particularly suitable for use in connection with ventral or inguinal hernia repair surgical procedures.

Figure 2:
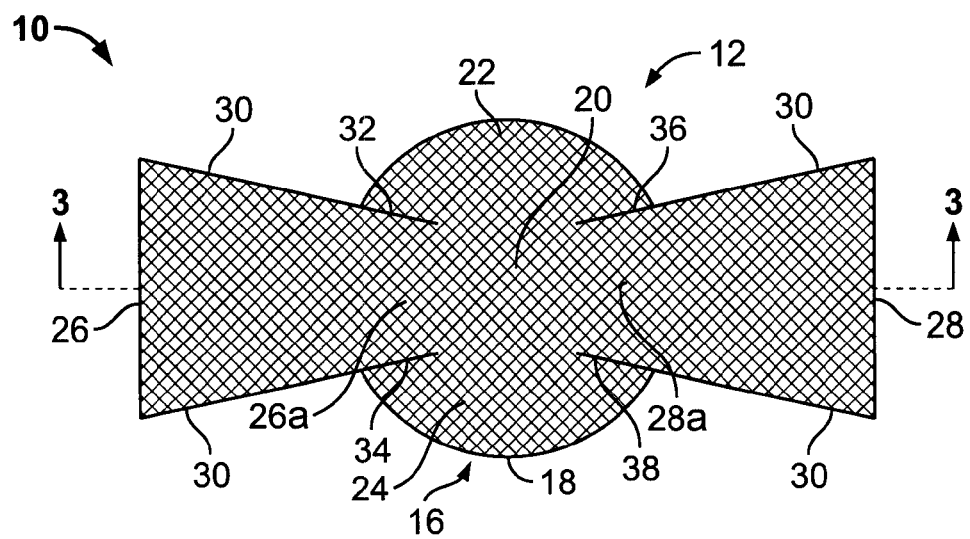
FIG. 2 is a top plan view of the implant shown in FIG. 1, the implant being illustrated in its substantially planar configuration.

Still referring to FIG. 1, the body 12 includes a base section 16 having an outer perimeter 18, a central or inner portion 20 and a plurality of arc-shaped outer portions 22, 24. The body 12 is also provided with a plurality of appendages or wings 26, 28, each of which has a pair of opposed edges 30 and projects radially outwardly from the inner portion 20 of the base section 16 in substantially opposite directions. Moreover, non-intersecting cuts 32, 34, 36, 38 (see FIG. 2) are made in the base section 16. More particularly, each of the cuts 32, 34, 36, 38 projects from the outer perimeter 18 of the body 12 and terminates at the inner portion 20 such that at least a portion (see element labeled as "26a" and "28a" in FIG. 2) of each of the appendages 26, 28 extends or is cut into the base portion 16. Because the entire body 12 is made from a single, one-piece sheet, the base section 16 and the appendages 26, 28 are formed integrally and/or contiguously with one another. That is, each of the appendages 26, 28 is connected to the base section 16 seamlessly (i.e., without any joint therebetween), thereby enhancing the overall structural integrity and strength of the implant 10.

Figure 3:
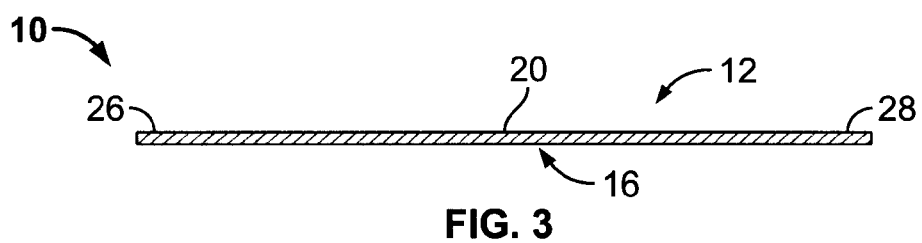
FIG. 3 is a view, taken along section line 3-3 and looking in the direction of the arrows, of the implant shown in FIG. 2.
Figure 4:
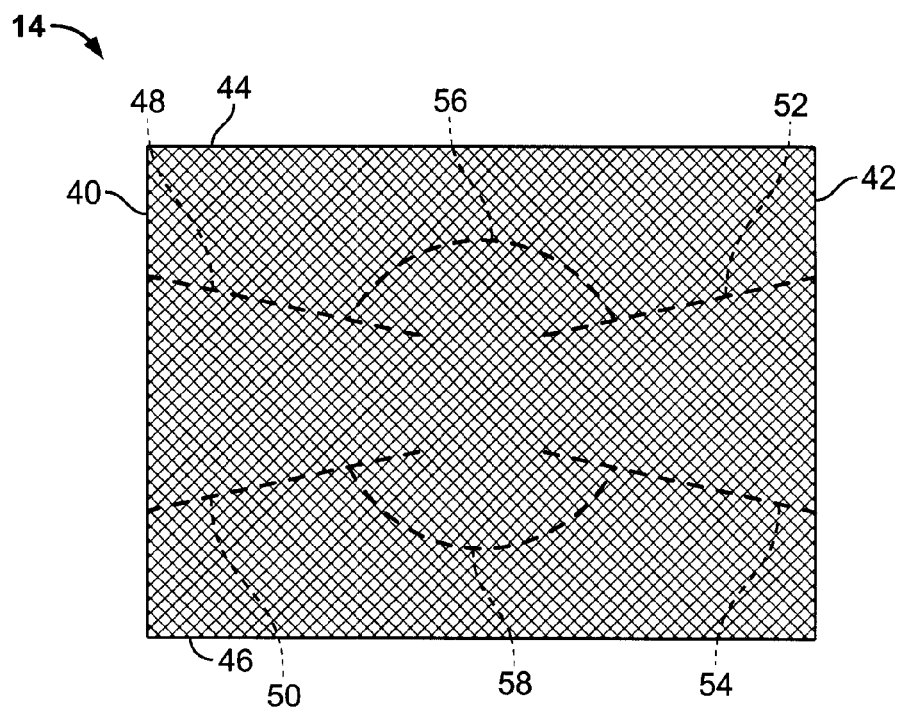
FIG. 4 is a schematic view of a sheet used in making the implant shown in FIGS. 1-3.
Figure 5:
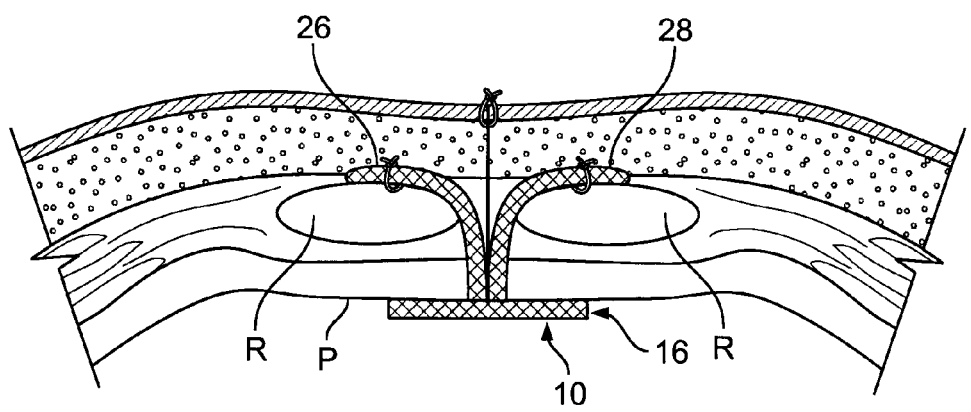
FIG. 5 is an in-use view of the implant shown in FIG. 1.

Referring to FIG. 4, the sheet 14 is made from a flexible material so as to provide sufficient flexibility to the body 12. As a result, each of the appendages 26, 28 is movable relative to the base section 16. In such circumstances, the appendages 26, 28 and the base section 16 can be positioned substantially coplanar relative to one another such that the body is oriented in its substantially two-dimensional (i.e., planar or flat) configuration (see FIGS. 2 and 3). In use, each of the appendages 26, 28 can be deflected at an angle from the base section 16 such that the overall body 12 is provided with a three-dimensional configuration (see FIG. 1). In this three-dimensional configuration, the appendages 26, 28 can be used to secure the implant 10 in place during a surgical procedure or at a repair site. For instance, when the implant 10 is used to repair a hernia associated with a rectus muscle R (see FIG. 5), the base section 16 of the implant 10 can be applied to a peritoneum P in a manner similar to a conventional intraperitoneal onlay mesh, while the appendages 26, 28 can be affixed to the top of the rectus muscle R. In this application, the base section 16 may need to be affixed to or at the peritoneum P to prevent same from being pulled through the hole. If the base section 16 is provided with a reinforcing layer (discussed in greater detail below), no such affixation would be necessary.

In order to fabricate the implant 10, the sheet 14 (see FIG. 4) is prepared from a conventional material (not shown) suitable for use in making hernia repair implants such that the sheet 14 is provided with a predetermined size and shape (e.g., a rectangular sheet having a pair of 8 cm sides 40, 42 and a pair of 11 cm sides 44, 46). The sheet 14 is then cut in a plurality of locations along the sides 40, 42, 44, 46 of the sheet 14 so as to form the appendages 26, 28 of the implant 10. For instance, a first substantially straight cut (indicated by broken lines 48 in FIG. 4) is made from the side 40 and terminates at a preselected location in the sheet 14 (e.g., 3 cm from the side 44 and 4.5 cm from the side 40), while a second substantially straight cut (indicated by broken lines 50 in FIG. 4) is made from the side 40 and terminates at a preselected location in the sheet 14 (e.g., 3 cm from the side 46 and 4.5 cm from the side 40). The starting points of the first and second cuts 48, 50 at the side 40 are separated from one another by a predetermined distance (e.g., at least 2 cm) and can be spaced apart equally from the midpoint of the side 40. The first and second cuts 48, 50 form the appendage 26. Third and fourth substantially straight cuts (indicated by broken lines 52, 54 in FIG. 4) are made from the side 42 in a fashion similar to that of the first and second cuts 48, 50 to form the appendage 28 of the implant 10.

After the cuts 48, 50, 52, 54 are made, arcuate cuts (indicated by broken lines 56, 58 in FIG. 4) are made in the sheet 14 to form the base section 16. More particularly, the arcuate cut 56 extends from the cut 48 to the cut 52, while the arcuate cut 58 extends from the cut 50 to the cut 54. In one embodiment, the arcuate cuts 56, 58 are provided with an identical radius (e.g., 2.5 cm) and share a common center point. In another embodiment, the arcuate cuts 56, 58 can be provided with differing diameters and/or can have different center points. The straight cuts 48, 50, 52, 54 and the arcuate cuts 56, 58 can be cut either sequentially or concurrently with the use of a convention tool (e.g., a punch or a die). Once the straight cuts 48, 50, 52, 54 and the arcuate cuts 56, 58 are made, portions of the sheet 14 beyond the borders of the appendages 26, 28 and the base section 16 are removed, leaving only the implant 10.

The sheet 14 can be made from any suitable material used for making hernia repair implants. For instance, the sheet 14 may be made from a film (e.g., "Monocryl" (Polyglecaprone 25, copolymer of glycolide and [epsilon]-caprolactone, Ethicon)) or a mesh (e.g., meshes sold by Ethicon, Inc. under the trademarks ULTRAPRO and PROLENE). Meshes may be knitted, woven or non-woven and may be made from an absorbable material (e.g., poliglecaprone 25, PDS and Panacryl) or a non-absorbable material (e.g., polypropylene, Teflon and Pronova) or a combination thereof. The sheet 14 may also be made from a porous or non-porous (i.e., impervious) material.

Although not necessary, the implant 10 may include additional layers of materials to provide the implant 10 with desirable tissue interface characteristics, such as enhanced rigidity, adhesion prevention, and antimicrobial and therapeutics to aid in tissue healing. Such additional layers can be provided on or in predetermined parts of the body 12 or can be applied to the entire body 12 and/or may be incorporated into or be inherent to the two-dimensional sheet 14, which is used in making the implant 10. When one or more additional layers (e.g., a reinforcing layer) are included in the implant 10 to provide enhanced stiffness or rigidity, they may be applied to the base section 16 so as to maintain same in a substantially flat position.

It should be noted that the implant 10 of the present invention can have numerous modifications and variations. For instance, each of the appendages 26, 28 shown in FIG. 1 extends beyond the outer perimeter 18 of the base section 16. Alternatively, one or both of the appendages 26, 28 can be made such that it terminates at or short of the outer perimeter 18 of the base section 16. Moreover, the specific dimensions of the implant 10 mentioned above are provided for illustration purposes only and do not therefore limit the scope of the present invention. Accordingly, the implant 10 can be provided with any suitable size or shape different from those specifically illustrated herein. By way of example, although the appendages 26, 28 are illustrated in FIG. 1 as having a flaring shape (i.e., the width of the appendages 26, 28 increases as they extend outwardly from the inner portion 20), they can be provided with a different shape (e.g., a tapering shape or a shape having an uniform width).

Figure 6:
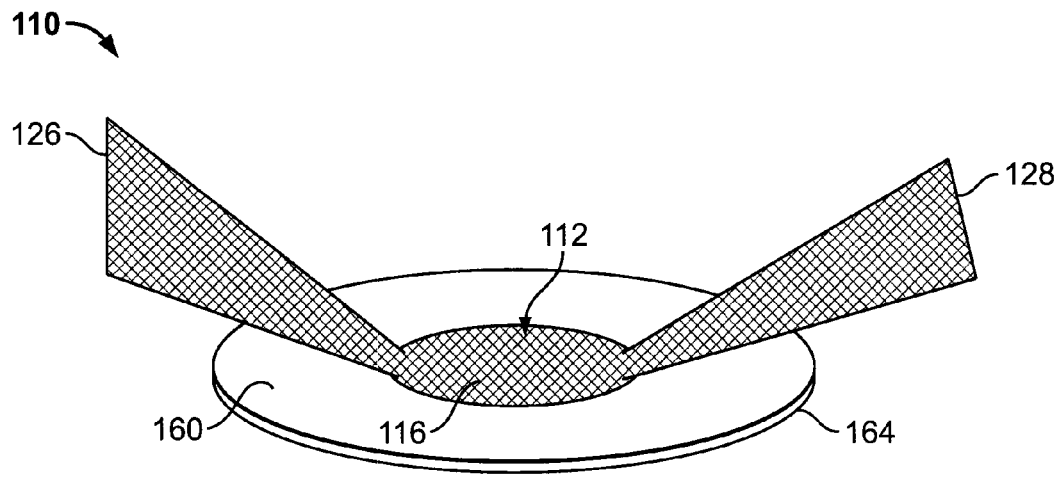
FIG. 6 is a perspective view of a hernia repair implant constructed in accordance with a second embodiment of the present invention.
Figure 7:
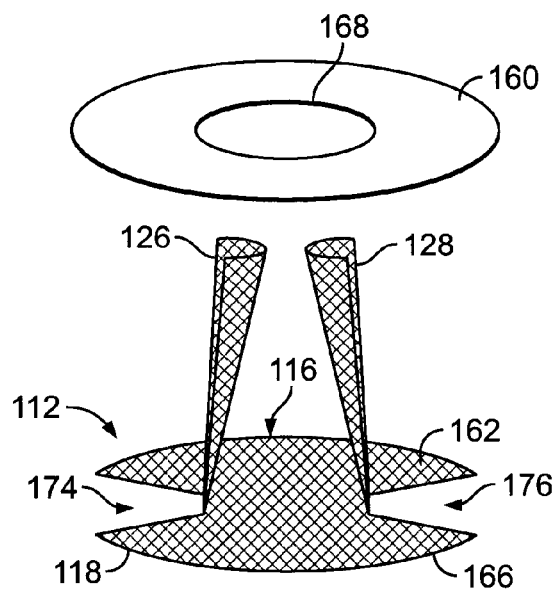
FIGS. 7 and 8 are sequential, schematic views illustrating a process for making the implant shown in FIG. 6.
Figure 8:
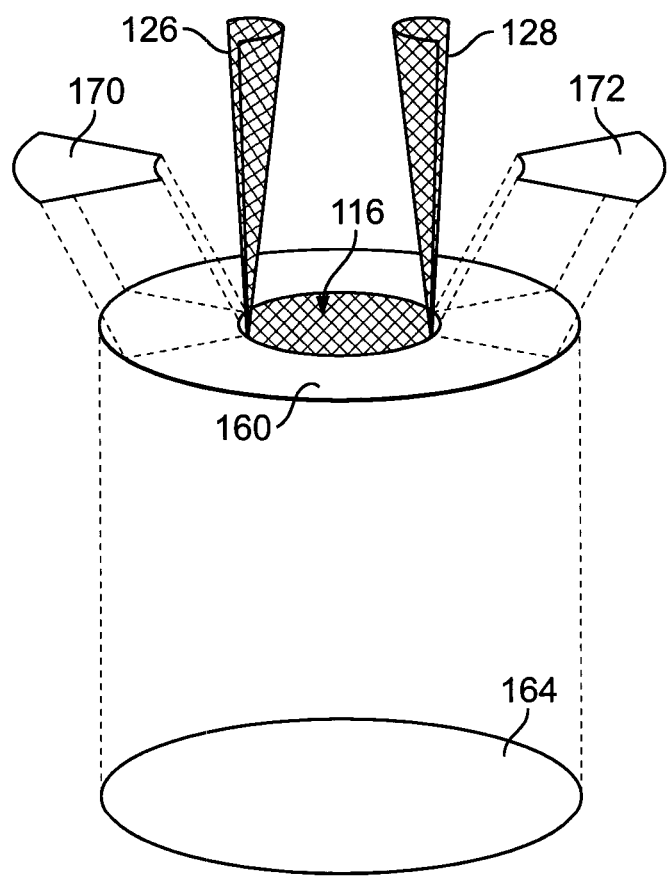

FIGS. 6-8 depict a second embodiment of the present invention. Elements illustrated in FIGS. 6-8, which correspond, either identically or substantially, to the elements described above with respect to the embodiment of FIGS. 1-5, have been designated by corresponding reference numerals increased by one hundred. Unless otherwise stated, the embodiment of FIGS. 6-8 is constructed, assembled and used in the same basic manner as the embodiment of FIGS. 1-5.

With reference to FIG. 6, a hernia repair implant 110 constructed in accordance with a second embodiment of the present invention is provided with a body 112, which is made in a manner basically identical to that of the body 12 of the embodiment shown in FIG. 1. Accordingly, the body 112 has the same construction as the body 12 and therefore includes a base section 116 and a pair of appendages or wings 126, 128 extending radially outwardly from the base section 116. Like the base section 16 of the embodiment of FIG. 1, the base section 116 has an outer perimeter 118 (see FIG. 7).

The implant 110 also includes a layer 160 (see FIGS. 6 and 7) attached to one side 162 (see FIG. 7) of the base section 116. The layer 160, which has a ring shape, can be made from any suitable material (e.g., polydioxanone or poliglecaprone 25) to provide enhanced stiffness to the base section 116. Another layer 164 (see FIGS. 6 and 8), which is in a circular shape, is attached to an opposite side 166 (see FIG. 7) of the base section 116. The layer 164 can be made from any suitable material (e.g., oxidized regenerated cellulose, such as absorbable hemostats or adhesion barriers sold by Ethicon, Inc. under the trademark SURGICEL NU-KNIT or INTERCEDD or synthetic absorbable films like Monocryl films or ePTEE films) for providing hemostatic and adhesion preventing characteristics to the implant 110. The layers 160 and 164 are attached only to the base section 116 such that the appendages 126, 128 are freely movable relative to the base section 116. In this manner, the implant 110 can be oriented in a substantially two-dimensional (i.e., flat or planar) configuration or be oriented in a three-dimensional configuration when implanted in a repair site.

In order to make the implant 110, the body 112 is prepared in the manner described above in connection with the body 12 of the embodiment shown in FIG. 1. The appendages 126, 128 are then passed through a circular opening 168 (see FIG. 7) formed in the layer 160 so as to allow the layer 160 to rest on the remaining flat surface of the body 112 (i.e., the base section 116). The layer 160 has a diameter (e.g., 5 cm) that corresponds to that of the base section 116 such that it does not extend beyond the outer perimeter 118 of the base section 116. Also, the circular opening 168 is provided with a sufficient diameter (e.g., 3 cm) so as not to interfere with the movement of the appendages 126, 128. Backing papers 170, 172 (see FIG. 8) are placed between the layer 160 and the appendage 126 and between the layer 160 and the appendage 128, respectively, to prevent the appendages 126, 128 from sticking to the layer 160 during a subsequent heat fusing process. The layer 164 is also applied to the side 166 of the body 112 (see FIG. 8). Like the layer 160, the layer 164 is provided with a diameter (e.g., 5 cm) that corresponds to that of the base section 116 such that it does not extend beyond the outer perimeter 118 of the base section 116. The entire assembly of the body 112, the layer 160, 164 and the backing papers 170, 172 is then held in a press at a predetermined temperature (e.g., 110° C.) for a preset time (e.g., 5 seconds). After cooling, the backing papers 170, 172 are removed from the implant 110. When fabricated in the manner described above, the layers 160 and 162 span across and hence close off open slots 174, 176 (see FIG. 7) which are formed in the base section 116 of the implant 110 by the appendages 126, 128, respectively.

It should be noted that the implant 110 of the present invention can have numerous modifications and variations. For instance, the layer 160 or the layer 164 can be eliminated from the implant 110. Moreover, both of the layer 160 and the layer 164 can be made from a stiffness-adding material to provide additional stiffness to the base section 116. In addition, the layer 160 and/or the layer 164 can be affixed to the base section 116 via other means (e.g., ultrasonic welding, etc.) or be formed by other conventional processes, rather than by attaching discrete films to the body 112 of the implant 110 as described above. By way of example, the layer 160 and/or the layer 164 can be formed by a solvent casting process using a suitable solution. Moreover, additional materials, such as antimicrobial agents, can be included in the implant 110. Further, the specific dimensions of the implant 110 mentioned above are provided for illustration purposes only and do not therefore limit the scope of the present invention.

The overall integrity of the implant 110 was tested by inserting same into a 3.5 cm hole that was formed in a 5 mm thick plastic board. To insert the implant 110 into the hole, it was first folded. The appendages 126, 128 were extended through the hole and were pulled upon a number of times using a spring balance. Ultimately, the implant 110 was pulled out. The average force was between 500 g to 1 Kg. In all tests, the implant remained substantially intact.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined in the appended claims.

I claim:

1. A hernia repair implant comprising:
a body having a base section, which includes an outer perimeter and a central portion positioned within said outer perimeter, and which is sized and shaped so as to be applied proximate a hole at a hernia site and remain in a substantially flat position so as to inhibit said base section from being pulled through the hole, and
a securing member, including at least one appendage connected to said base section, for securing said base section in place at the hernia site, wherein said body includes a plurality of cuts extending from said outer perimeter into said body such that said at least one appendage has a portion extending into said base section,
said body being made from a flexible material such that said at least one appendage is movable relative to said base section, and such that said at least one appendage can be affixed to a tissue remote from the hernia site, said body being constructed from a single, one-piece sheet such that said at least one appendage is connected to said base section seamlessly without any joint therebetween, said at least one appendage including a first appendage, which extends from a first point proximate a first side of said central portion and beyond said outer perimeter of said base section, and a second appendage, which extends from a second point proximate a second side of said central portion opposite said first side and beyond said outer perimeter of said base section, said flexible material extending across and throughout said central portion between said first point and said second point such that said central portion is formed entirely by said flexible material; and
a reinforcing layer attached to said base section for maintaining the substantially flat position of said base section at the hernia site.

2. The implant of claim 1, wherein said base section has a first side and a second side, said reinforcing layer having an opening therethrough and attached to said first side of said base section, said at least one appendage extending through said opening of said reinforcing layer such that it is freely movable relative to said base section.

3. The implant of claim 2, wherein said body includes a second layer attached to said second side of said base section.

4. The implant of claim 3, wherein said base section includes first and second slots formed by said first and second appendages, respectively, said first and second layers spanning across said first and second slots and hence closing off said first and second slots.

5. The implant of claim 3, wherein said second layer provides said implant with a tissue interface characteristic that is selected from one of the following characteristics: enhanced rigidity, adhesion prevention, and antimicrobial and therapeutics to aid in tissue healing.

6. The implant of claim 1, wherein said reinforcing layer is attached to said base section such that it does not interfere with the movement of said at least one appendage relative to said base section.

7. The implant of claim 1, wherein said first and second appendages each extend beyond said outer perimeter when said base section is oriented in its said substantially flat position.

8. The implant of claim 1, wherein each of said cuts extends from said outer perimeter of said body to said central portion of said base portion.

9. The implant of claim 1, wherein said first and second appendages extend radially outwardly from said base section in opposite directions.

10. The implant of claim 1, wherein said base section is sized and shaped so as to block the hole at the hernia site.

11. The implant of claim 1, wherein said central portion is positioned entirely within said outer perimeter.

* * * * *